United States Patent [19]

Buchanan

[11] Patent Number: 4,708,651

[45] Date of Patent: Nov. 24, 1987

[54] ENDODONTIC ROOT CANAL FILE BENDING PLIERS

[76] Inventor: L. Stephen Buchanan, 179 Hermosillo Rd., Montecito, Calif. 93108

[21] Appl. No.: 899,342

[22] Filed: Aug. 22, 1986

[51] Int. Cl.$^4$ .............................................. A61C 3/00
[52] U.S. Cl. .................................... 433/157; 433/72; 433/102
[58] Field of Search .................. 433/72, 77, 102, 141, 433/156, 157

[56] References Cited

U.S. PATENT DOCUMENTS

| | | | |
|---|---|---|---|
| 1,108,493 | 8/1914 | Federspiel | 433/224 |
| 3,142,484 | 7/1964 | Press | 140/106 |
| 3,360,018 | 12/1967 | Lindsay | 140/106 |
| 3,692,069 | 9/1972 | Clendennen et al. | 140/106 |
| 4,184,259 | 1/1980 | Sosnay | 433/4 |
| 4,399,844 | 8/1983 | Kober et al. | 140/106 |
| 4,536,159 | 8/1985 | Roane | 433/224 |

FOREIGN PATENT DOCUMENTS 198521  8/1967  U.S.S.R. .................................. 433/4

OTHER PUBLICATIONS

Orthopli Catalog, p. 17.

*Primary Examiner*—Robert Peshock
*Attorney, Agent, or Firm*—Henry M. Bissell

[57] ABSTRACT

A tool for use in bending root canal files is disclosed which grips a file between an upper jaw with a plastic insert to protect the surface of the file and a lower jaw having a file bending anvil thereon. The file bending anvil has ten specific bending diameters thereon, and the file is bent by gripping it in the jaws and wrapping it around the desired specific bending curve. A template having circles thereon corresponding to the specific bending diameters on the file bending anvil may be used with an X-ray of the root canal to select the appropriate bending diameter for the file.

20 Claims, 7 Drawing Figures

U.S. Patent   Nov. 24, 1987   4,708,651 ic apparatus and, more particularly, to a tool for conveniently bending root canal files to selected curvatures of different radii within a predetermined range to allow the root canal files to precisely fit the curved portions of a root canal.

ENDODONTIC ROOT CANAL FILE BENDING PLIERS

BACKGROUND OF THE INVENTION

1. Field of the Invention

The present invention relates generally to orthodontic apparatus and, more particularly, to a tool for conveniently bending root canal files to selected curvatures of different radii within a predetermined range to allow the root canal files to precisely fit the curved portions of a root canal.

2. Description of the Prior Art

Root canal files or reamers are used in the cleaning of material present in the root canal of a human tooth and enlarging the root canal so that it may be filled. In the performance of a root canal procedure, a hole is first cut in the crown or exposed portion of the tooth, typically either in the biting surface of the tooth, for posterior teeth, or in the side of the tooth on the interior of the jaw for incisor teeth. Root canal files are then used to clean out the material present in the root canal, and to shape the root canal so that a tapered filling material may be inserted into the root canal to fill it.

When a root canal is being cleaned and shaped, a series of files increasing in size is used to gradually enlarge the root canal. A complete set will include a number of different sizes, with as many as eleven files in a set typically being used. The files are held between the thumb and forefinger of one hand by the dentist. Each file has one or more cutting surfaces thereon, with the cutting surfaces typically being in a spiral configuration. An examplary description of such a file may be found in U.S. Pat. No. 4,536,159 of Roane.

Unlike the files, root canals are seldom straight. If the files which are used deviate substantially from the original curvature of the root canal, the tooth may be irreversibly damaged. If the file is too straight and cuts through the side of the root in which the canal is located, which is referred to as a perforation of the root, the tooth must then be removed. If the tip of the file does not follow the curvature of the canal and bores a passage branching out from the root canal, which is referred to as ledging, surgical correction of the problem is necessitated. For a more detailed discussion of perforation and ledging, see my U.S. patent application Ser. No. 899,419, entitled Anti-Curvature Dental Root Canal Shaping File and filed concurrently with the present application. That application is hereby incorporated herein by reference.

It is therefore apparent that the files should be accurately bent prior to insertion into the root canal and use of the files to enlarge the root canal. Such bending of the files has typically been done crudely with hemostat pliers, tweezers or similar tool. Since the cutting edges of the files are very small and highly precise, great care must be taken to avoid damaging the file. It will be appreciated that it is relatively difficult to properly perform a very precise bend in a file with such inappropriate tools.

While the technology of bending metal includes a number of tools for bending leads of electrical components, such as U.S. Pat. No. 3,692,069, to Clendennen et al., and U.S. Pat. No. 4,399,844, to Kober et al., such tools are useless when it comes to making a precise yet delicate bend in a root canal file. The only art relating to dental bending tools is found in U.S. Pat. No. 1,108,493, to Federspiel, which discloses pliers for use in shaping loops of orthodontia wire. All dental pliers are relatively brute force instruments, for use in making curves in metal rather than for configuring root canal files to precisely fit the curvature of a root canal.

It is therefore apparent that there exists a substantial need for a tool which will be capable of imparting precise curves of various selected radii to any of a series of root canal files without damaging or distorting the cutting surfaces of the file. The solution to this need should also be relatively inexpensive, and capable of being used with all sizes of root canal files. Finally, a potential solution must also remedy the problems mentioned above without incurring relative disadvantage.

SUMMARY OF THE INVENTION

The disadvantages and limitations of the background art discussed above are overcome by the present invention. This invention involves a tool having two arms fastened together at one end of each of the arms, one of which arms flexes to allow the ends of the two arms not connected together to move closer together. As the ends of the two arms move together, the tip of the cutting surface of a root canal file is gripped between surfaces on the free ends of the two arms, the first of which surfaces includes a clamp insert made of a softer material, such as plastic. The use of this softer clamp insert protects both the cutting surface of the file from being damaged and the tip of the file from being distorted into an eccentric cross-section.

The second gripping surface of the tool is used as a file bending anvil or form that the file may be bent around, with a number of curves of different radii delineated on the anvil to present to the file different bending radii which may be used to form any desired curvature in the file. Since the file is typically held by the tip, the file may be wrapped around the desired curve on the file bending anvil to create a corresponding curve in the file. Of course, the file could be gripped at various locations along its cutting surface if the curvature desired in the file begins at a location other than the tip of the file.

The various bending radii (or diameters) are identified on the tool, and are keyed to a precision template accompanying the tool. The template has thereon a number of circles, each circle having the curvature of one of the curves of different radii on the second surface of the tool. The template is overlaid upon X-rays of the root canal of a tooth to determine the radius of curvature needed on the file. The file may then be given the appropriate curvature with a relatively high degree of accuracy and the quantification of the curvature of the root canal at selected points may be entered on X-rays or charts for reference.

In the preferred embodiment, the file bending anvil of the second surface of the tool has smooth transitions between the various different bending radii. An alternative embodiment has step-wise changes in the bending radii on the file bending anvil. The second surface also preferably includes a flat file-straightening anvil surface which may be used to straighten files which have been previously bent.

By using the tool of the present invention, a file may be given a highly accurate radius of curvature without either damaging the cutting surface of the file or imparting an eccentric shape to the portion of the file gripped in the tool. Complex curves may be placed in a file, and by using the template the file may be precisely shaped to fit the curvature of a root canal taken from an X-ray.

Since the file may be better curved using the present invention, occurrences of perforating the root canal and ledging in the root canal will be minimized.

The tool of the present invention may be economically manufactured, and one tool will work with a variety of different size and different type files. In addition, the present invention accomplishes all of the above advantages without incurring any disadvantage whatsoever.

BRIEF DESCRIPTION OF THE DRAWING

A better understanding of the present invention may be had from a consideration of the following detailed description, taken in conjunction with the accompanying drawing in which.

DETAILED DESCRIPTION OF THE PREFERRED EMBODIMENT

Figure 1:
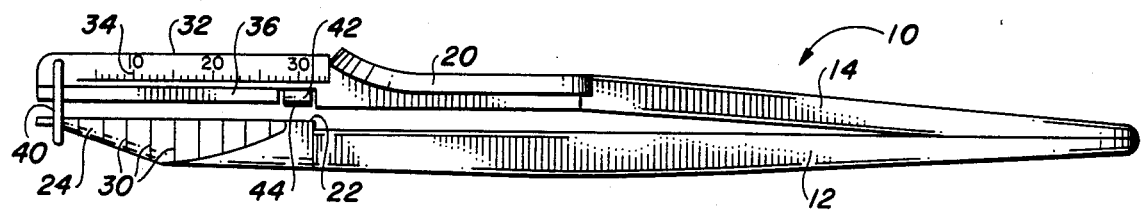
FIG. 1 is a side view of the tool of the present invention illustrating the surfaces which will grip a file to be curved.
Figure 2:
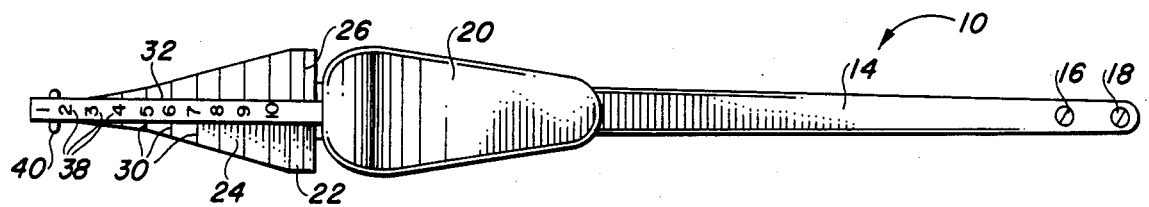
FIG. 2 is a top view of the tool shown in FIG. 1 showing the numbers on the top half of the tool referencing the lines on the file bending anvil of the lower jaw and indicating the curvature of the file bending anvil at these lines.
Figure 3:
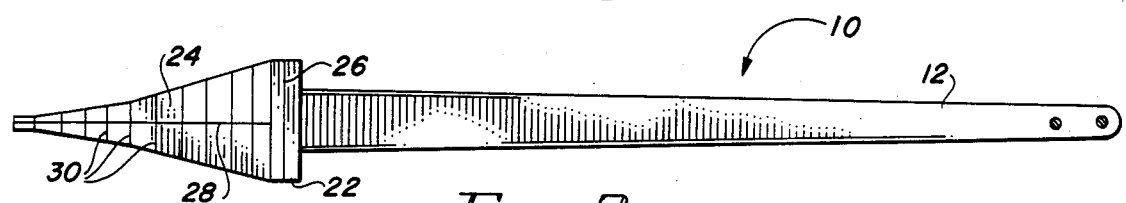
FIG. 3 is a top view of the lower half of the tool showing the file bending anvil and its reference lines.
Figures 5, 6:
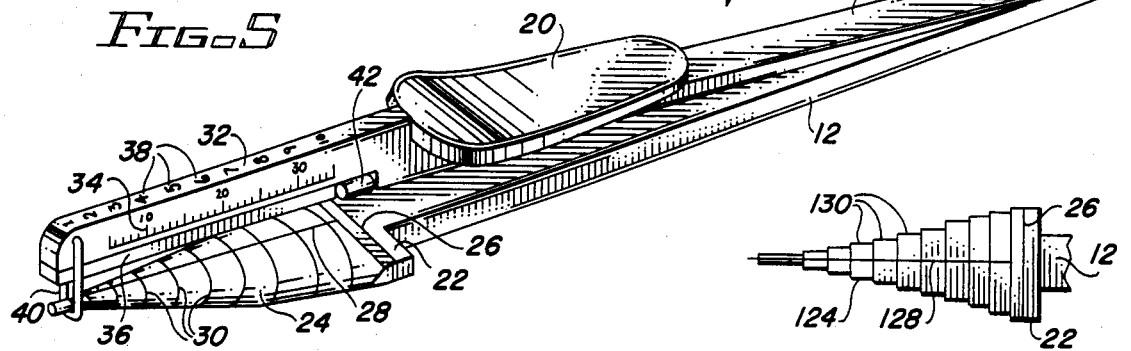
FIG. 5 is a perspective view of the tool shown in the previous figures.
FIG. 6 is a top view of an alternative embodiment of the file bending anvil having step-wise changes in bending radii.

One preferred embodiment of an endodontic file bending pliers 10 incorporating the teachings of the present invention is shown in FIGS. 1-5. The frame of the pliers 10 is made up of a rigid lower arm 12 and a flexible upper arm 14. The lower arm 12, for example, may be made of rigid steel, and the upper arm 14 may be made of spring steel. The upper arm 14 is fastened at one end to one end of the lower arm 12 by two screws 16, 18, as best shown in FIGS. 2 and 5, or by soldering or welding, as desired. The upper arm 14 has disposed thereon a thumb rest 20, and extends over the lower arm 12 and is normally spaced away from the lower arm 12 at the ends of the arms 12, 14 not fastened together.

The pliers 10 may be gripped in one hand (not shown) with the four fingers around the arm 12, with the thumb of the hand resting on the thumb rest 20. By pressing on the thumb rest 20 with the thumb, the arms 12, 14 may be brought closer together at the distal ends of the arms 12, 14 which are remote from the proximal ends which are fastened together by the screws 16, 18, for example.

At the end of the lower arm 12 are a file straightening anvil 22 and a file bending anvil 24. The file straightening anvil 22 is located first on the lower arm 12, and is a flat surface facing the upper arm 14. The file straightening anvil 22 has across it a mark 26 which is perpendicular to the arms 12, 14. This mark 26 is an indication where a file (not shown) would be placed to be straightened, as will become more evident below.

Figure 4:
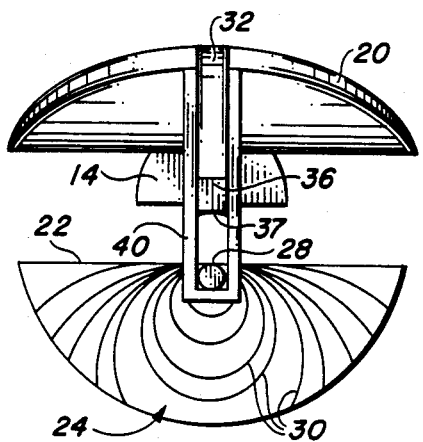
FIG. 4 is an end view of the tool of FIGS. 1 and 2 showing the file bending anvil and its reference lines.

The file bending anvil 24 is a smooth rounded surface which is characterized by ever decreasing radii of curvature at locations moving farther away from the end of the lower arm 12 to which the upper arm 14 is attached. All possible circular segments in the smooth rounded surface coincide in (are tangent to) a line 28 parallel to and facing the upper arm 14, as best shown in FIGS. 1, 4 and 5. On the file bending anvil 24, ten specific bending diameters are marked, several of which are identified by the reference numeral 30. These specific bending diameters are marked on the file being anvil 24, either by scoring the anvil 24 or by painting or otherwise providing an indication of the location of the diameters. They in effect represent ten forms around one of which a file may be bent to produce one of the ten specific curvatures characterized by the diameters.

The end of the upper arm 14 includes a file clamp jaw 32 extending over the file straightening anvil 22 and the file bending anvil 24. The file clamp jaw may have on the side thereof a millimeter gauge 34 for measuring endodontic files during treatment. The file clamp jaw 32 has on the underside thereof a plastic clamp insert 36 which extends over the line 28 on the file bending anvil 24. Both the file clamp jaw 32 and the plastic clamp insert 36 are parallel to the line 28 on the file bending anvil. When the thumb rest 20 is pressed, the plastic clamp insert 36 will therefore contact the line 28 on the file bending anvil 24. The insert 36 has a concave curved under-surface 37 for receiving the upper surface of the file bending anvil 24.

If a file (not shown) is placed between the plastic clamp insert 36 and the file bending anvil 24 along the appropriate specific bending diameter 30 before the thumb rest 20 is pressed, the file will be held, and may then be bent around the selected bending diameter 30. It will be appreciated by those skilled in the art that the plastic clamp insert 36 is soft enough to prevent the delicate file from being bent into an eccentric shape or having its cutting surface damaged.

The material the plastic clamp insert 36 is made of may vary, as long as it is sufficiently soft to protect a file. For example, hard silicone rubber could be used instead of plastic. The plastic clamp insert 36 is also replaceable, preferably sliding out the end of the upper arm 14. Referring to FIGS. 2 and 5, there are numerical identifications 38 on the top of the file clamp jaw 32 which correspond to the specific bending diameters 30 on the file bending anvil 24.

The arms 12, 14 are kept in alignment by a U-shaped clamp jaw guide 40, best shown in FIGS. 1 and 4. The lower part of the clamp jaw guide 40 envelopes the file bending anvil 24, with the smallest specific bending diameter extending beyond the clamp jaw guide 40, as shown in FIG. 2.

A plastic clamp roller 42 is mounted over the file straightening anvil 22 on the lower arm 12 by using a roller axle 44 on the upper arm 14. The roller 42 may then rotate, so a file (not shown) may be placed between the roller 42 and the file straightening anvil 22 on the reference line 26, and pulled while the thumb rest 20 is pressed down to straighten the file. This works quite well without damaging the file. The roller 42 may also be replaceable, like the clamp insert 36. The axle 44 is preferably made of stainless steel to resist corrosion and wear.

An alternative embodiment for the file bending anvil 24 is shown in FIG. 6. A file bending anvil 124 has step-wise changes in the specific bending diameters, with ten specific diameters again being present, some of which are indicated by the reference numeral 130. The bending diameters are all tangent to a line 128, which would be directly under the plastic clamp insert 36. The file straightening anvil 26 is again next to this alternative file bending anvil 124.

Figure 7:
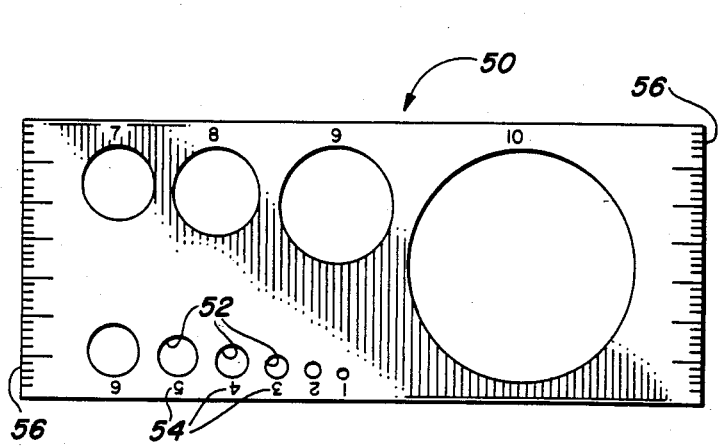
FIG. 7 shows a precision clear plastic template for measuring radius of curvature from an X-ray, which radius corresponds to the reference numbers on the tool as shown in FIG. 2.

Referring finally to FIG. 7, a clear plastic root canal curvature template 50 is shown. The template 50 has ten circles therein, some of which are marked by the reference numeral 52. These circles have diameters corresponding respectively to the diameters of the curved segments 30 of the bending anvil 24. Numerical identifications, some of which are indicated by the reference numeral 54, correspond to the numerical identifications of specific bending diameters 38 on the top of the file clamp jaw 32 (FIGS. 2 and 5). The template 50 may be used to measure the curvature of a root canal by overlaying the template on an X-ray (not shown) and determining which circle diameter 52 corresponds to the curvature of the root canal, thereby determining the appropriate bending diameter for bending a file. The template 50 also has millimeter markings 56 thereon, which may be used to measure the root canal as it appears on an X-ray conveniently and also the files which are to be used in preparing the root canal.

It may thus be appreciated that the present invention represents a substantial improvement in the art, by which files may be easily, conveniently, and accurately bent without damaging either the cutting surface of the file or otherwise deforming the file. The pliers 10 may be manufactured quite inexpensively, and is highly durable as well as being quite accurate and precise. It will work with a variety of different size and different type files, bending them all easily, even in complex curves or according to an X-ray. Occurrences of perforating the root canal and ledging in the root canal may be minimized through use of this tool.

Although there have been described above specific arrangements of an endodontic root canal file bending pliers in accordance with the invention for the purpose of illustrating the manner in which the invention may be used to advantage, it will be appreciated that the invention is not limited thereto. For example, features of the present invention may be embodied in a hinged hemostat-type of pliers, rather than the type of pliers which is depicted in the drawings, without departing from the scope of the present invention. Accordingly, any and all modifications, variations or equivalent arrangements which may occur to those skilled in the art should be considered to be within the scope of the invention as defined in the annexed claims.

What is claimed is:

1. An endodontic tool for bending root canal files, comprising:
   a rigid arm having a first end and a second end;
   a flexible arm attached at a first end thereof to said first end of said rigid arm, said flexible arm having a second end which extends over and is spaced away from said second end of said rigid arm;
   a first gripping surface located at said second end of said flexible arm and facing said first arm;
   a smooth rounded surface located at said second end of said rigid arm and facing said first gripping surface, said smooth rounded surface being characterized by ever decreasing radii of curvature at locations moving farther away from the first end of the rigid arm, the circular segments in said smooth rounded surface passing through a line parallel to and facing said first gripping surface, said line being a second gripping surface, said first gripping being brought into contact with said second gripping surface when said flexible arm is bent toward said rigid arm.

2. An endodontic tool as defined in claim 1 wherein said rigid arm is made of non-flexible steel and said flexible arm is made of spring steel and wherein the two arms are biased away from each other.

3. An endodontic tool as defined in claim 1 wherein said flexible arm is fastened to said rigid arm by screws.

4. An endodontic tool as defined in claim 1 wherein said first gripping surface comprises:
   a file clamp jaw mounted on the end of said rigid arm; and
   a clamp insert made of soft material and mounted on the side of said file clamp jaw facing said second gripping surface, said clamp insert protecting the cutting edges of a root canal file gripped between said first and second gripping surfaces.

5. An endodontic tool as defined in claim 4 wherein said soft material is one of the materials from the group consisting of plastic and silicone rubber.

6. An endodontic tool as defined in claim 4 wherein said file clamp jaw has numerical identifications on the top of said file clamp jaw opposite said rounded surface on said rigid arm, which numerical identifications correspond to a number of specific bending diameters on said smooth rounded surface.

7. An endodontic tool as defined in claim 4 wherein said file clamp jaw has on the side thereof a millimeter gauge for measuring endodontic files during treatment.

8. An endodontic tool as defined in claim 4 additionally comprising:
   a U-shaped clamp jaw guide for keeping the flexible and rigid jaws in alignment, the lower part of the clamp jaw guide enveloping the smooth rounded surface at the end remote from said first end of said rigid arm, where the radius of curvature of said smooth rounded surface is smallest.

9. An endodontic tool as defined in claim 1 wherein said smooth rounded surface has therein a plurality of step-wise changes in the specific radii of curvature, with a plurality of specific bending diameters being present, all of which intersect said line.

10. An endodontic tool as defined in claim 9 wherein there are ten step-wise changes and ten specific bending diameters.

11. An endodontic tool as defined in claim 1 wherein said smooth rounded surface has identifying indicia thereon to mark ten specific bending diameters.

12. An endodontic tool as defined in claim 11 additionally comprising in combination therewith:
   a precision template having ten circles of sizes corresponding to said ten specific bending diameters, which template may be used to measure the curvature of a root canal as determined by an X-ray, with the appropriate bending diameter being selected from the circle matching the curvature of the root canal.

13. An endodontic tool as defined in claim 12, wherein said template also has millimeter markings thereon, which may be used to measure an X-ray conveniently.

14. An endodontic tool as defined in claim 1 additionally comprising:

a thumb rest mounted on said flexible arm near said second end thereof, for forcing said flexible arm toward said rigid arm.

15. An endodontic tool as defined in claim 1 additionally comprising:

means for straightening a root canal file.

16. An endodontic tool as defined in claim 15 wherein said straightening means comprises:

a flat surface at said second end of said rigid arm, said flat surface facing said flexible arm; and a roller mounted for rotation on said flexible arm, said roller being brought into contact with said flat surface when said flexible arm is bent toward said rigid arm.

17. An endodontic tool as defined in claim 16 wherein said roller is made of plastic.

18. An endodontic tool for precisely bending a root canal file, comprising:

a first arm having a first end and a second end;

a second arm having a first end and a second end, said first end of said first arm being mechanically connected to said first end of said second arm, said second end of said first arm extending over and biased away from said second end of said second arm;

a file clamp jaw located at said second end of said second arm, said file clamp jaw facing said first arm;

a smooth rounded surface located at said second end of said first arm and facing said file clamp jaw, said smooth rounded surface being characterized by ever decreasing radii of curvature at locations moving farther away from the first end of the first arm, all possible circular segments in said smooth rounded surface coinciding in a line parallel to and facing said file clamp jaw, said line being a second jaw, said file clamp jaw being brought into contact with said second jaw when said first arm is forced toward said second arm; and a plastic clamp insert made of soft material and mounted on the side of said file clamp jaw facing said first arm, said plastic clamp insert protecting the cutting edges of a root canal file gripped between said file clamp jaw and said file bending anvil.

19. An endodontic root canal file bending tool, comprising:

a rigid arm having a first end and a second end;

a flexible arm attached at a first end thereof to said first end of said rigid arm, said flexible arm having a second end which extends over and is biased away from said second end of said rigid arm;

a first gripping surface mounted at said second end of said flexible arm and facing said first arm;

a second gripping surface mounted at said second end of said rigid arm, said first gripping surface being brought into contact with said second gripping surface when said flexible arm is urged toward said rigid arm; and a plurality of bending forms in orthogonal contact with said second surface, said plurality of bending forms representing a plurality of specific bending radii about which a root canal file may be bent.

20. A method of precisely bending a root canal file, comprising:

providing a rigid arm having a first end and a second end;

attaching a flexible arm at a first end thereof to said first end of said rigid arm, said flexible arm having a second end which extends over and is biased away from said second end of said rigid arm;

locating a first surface for gripping a root canal file at said second end of said flexible arm, said first surface being oriented toward said second end of said first arm;

forcing said flexible arm toward said rigid arm to grip a root canal file between said first gripping surface and a second gripping surface, said second gripping surface being a line on a smooth rounded surface, said line being parallel to and facing said first gripping surface, said smooth rounded surface being located at said second end of said rigid arm and facing said first gripping surface, said smooth rounded surface being characterized by ever decreasing radii of curvature at locations moving farther away from the first end of the rigid arm, all possible circular segments in said smooth rounded surface coinciding in said line; and bending said root canal file around one of a plurality of specific bending diameters.

* * * * *